US011918802B2

(12) United States Patent
Offutt et al.

(10) Patent No.: US 11,918,802 B2
(45) Date of Patent: Mar. 5, 2024

(54) FORAMINA-FILLING IMPLANTABLE MEDICAL LEAD

(71) Applicant: MEDTRONIC, INC., Minnepolis, MN (US)

(72) Inventors: Sarah J. Offutt, Minneapolis, MN (US); Juan G. Hincapie, Minneapolis, MN (US); Jerel K. Mueller, Minneapolis, MN (US); Robert T. Sandgren, Minneapolis, MN (US); Katie Bittner, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 288 days.

(21) Appl. No.: 17/156,856

(22) Filed: Jan. 25, 2021

(65) Prior Publication Data
US 2021/0228868 A1 Jul. 29, 2021

Related U.S. Application Data

(60) Provisional application No. 62/966,327, filed on Jan. 27, 2020.

(51) Int. Cl.
*A61N 1/05* (2006.01)
*A61N 1/36* (2006.01)
*A61N 1/372* (2006.01)
*A61N 1/375* (2006.01)

(52) U.S. Cl.
CPC ....... *A61N 1/0558* (2013.01); *A61N 1/36062* (2017.08); *A61N 1/37211* (2013.01); *A61N 1/37518* (2017.08)

(58) Field of Classification Search
CPC .............. A61N 1/0558; A61N 1/36062; A61N 1/37518
See application file for complete search history.

(56) References Cited

U.S. PATENT DOCUMENTS

| 5,484,445 | A | 1/1996 | Knuth | |
|---|---|---|---|---|
| 6,575,979 | B1 | 6/2003 | Cragg | |
| 6,847,849 | B2* | 1/2005 | Mamo | A61N 1/0551 607/117 |
| 8,019,443 | B2 | 9/2011 | Schleicher et al. | |
| 8,892,214 | B2* | 11/2014 | Bonde | A61B 5/6848 607/117 |
| 9,623,253 | B2 | 4/2017 | Perryman et al. | |
| 2004/0088021 | A1 | 5/2004 | Cameron et al. | |
| 2007/0255368 | A1* | 11/2007 | Bonde | A61N 1/0558 607/116 |

(Continued)

*Primary Examiner* — Eric D. Bertram
(74) *Attorney, Agent, or Firm* — Shumaker & Sieffert, P.A.

(57) ABSTRACT

Examples of implantable medical leads or implantable medical systems with implantable medical leads to be anchored to a sacrum are disclosed. The implantable medical leads include a lead body having a distal portion. A fixation mechanism is coupled to the distal portion. An electrode array is mechanically coupled to the fixation mechanism. In one example, the electrode array is directly coupled to the fixation mechanism. The electrode array is electrically coupled to the lead body and configured to generate a stimulation field. The fixation mechanism is configured to anchor the implantable medical lead to a sacrum and effect the stimulation field in a foramen of the sacrum.

19 Claims, 6 Drawing Sheets

(56) References Cited

U.S. PATENT DOCUMENTS

| | | | |
|---|---|---|---|
| 2007/0255379 A1* | 11/2007 | Williams | A61N 1/05 607/116 |
| 2009/0248095 A1* | 10/2009 | Schleicher | A61N 1/0558 607/116 |
| 2018/0256906 A1 | 9/2018 | Pivonka et al. | |
| 2019/0290923 A1 | 9/2019 | Yeh et al. | |
| 2019/0357847 A1 | 11/2019 | Franke et al. | |

\* cited by examiner

FORAMINA-FILLING IMPLANTABLE MEDICAL LEAD

CROSS-REFERENCE TO RELATED APPLICATION

This Non-Provisional Utility Application claims benefit to U.S. Provisional Application No. 62/966,327, filed Jan. 27, 2020, titled "FORAMINA-FILLING IMPLANTABLE MEDICAL LEAD," the entirety of which incorporated herein by reference.

BACKGROUND

The present disclosure relates generally to a method and apparatus that allows for electrical stimulation of body tissue, particularly sacral nerves. More specifically, the present disclosure relates to an implantable medical electrical lead having a stimulation electrode adapted to be implanted in a sacral foramen near the sacral nerve to stimulate of a bundle of sacral nerve fibers and adapted to provide chronic stability of the stimulation electrode in the sacral foramen. Moreover, the present disclosure relates to the method of implantation and anchoring of the medical electrical lead electrodes in operative relation to a selected sacral nerve to allow for stimulation within the sacral foramen.

Implantable electrical stimulation systems are therapeutic in a variety of diseases and disorders. For example, spinal cord stimulation systems have been used as a therapeutic modality for treatment of chronic pain syndromes. Deep brain stimulation has been useful for treating refractory chronic pain syndromes, movement disorders, and epilepsy. Peripheral nerve stimulation has been used to treat chronic pain syndrome and pelvic floor disorders. Other applications are under investigation.

Pelvic floor disorders such as urinary incontinence, urinary urge/frequency, urinary retention, pelvic pain, bowel dysfunction (constipation, diarrhea), and sexual dysfunction are bodily functions influenced by the sacral nerves. Specifically, urinary incontinence is the involuntary control over the bladder that is exhibited in various patients. Incontinence is primarily treated through pharmaceuticals and surgery. Pharmaceuticals may not adequately resolve the issue and can cause unwanted side effects, and a number of the surgical procedures have a low success rate and are not reversible. Several other methods have been used to control bladder incontinence, for example, vesicostomy or an artificial sphincter implanted around the urethra. These solutions also have drawbacks. In addition, some disease states do not have adequate medical treatments.

The organs involved in bladder, bowel, and sexual function receive much of their control via the second, third, and fourth sacral nerves, commonly referred to as S2, S3 and S4 respectively. Electrical stimulation of these various nerves has been found to offer some control over these functions. Several techniques of electrical stimulation may be used, including stimulation of nerve bundles within the sacrum. The sacrum, generally, is a large, triangular bone situated at the lower part of the vertebral column, and at the upper and back part of the pelvic cavity. The spinal canal runs throughout the greater part of the sacrum. The sacrum is perforated by the anterior and posterior sacral foramina that the sacral nerves pass through.

Neurostimulation leads have been implanted on a temporary or permanent basis having a stimulation electrode (at least one stimulation electrode) positioned on and near the sacral nerves to provide partial control for bladder incontinence. Temporary sacral nerve stimulation is accomplished through implantation of a temporary neurostimulation lead extending through the skin and connected with a temporary external pulse generator. A permanent neurostimulator is implanted if stimulation is efficacious and it is possible to do so in the particular patient. Permanent implantation is accomplished by implanting a permanent neurostimulation lead, extending the proximal portion of the lead body subcutaneously, and connecting its proximal end with an implantable pulse generator, or IPG, implanted subcutaneously.

In one example, a lead bearing a distal stimulation electrode is percutaneously implanted through the dorsum and the sacral foramen of the sacral segment S3 for purposes of selectively stimulating the S3 sacral nerve. The lead is advanced through the lumen of a hollow spinal needle extended through the foramen, and the single distal tip electrode is positioned adjoining the selected sacral nerve. Stimulation energy is applied through the lead to the electrode to test the nerve response. The electrode is moved back and forth to locate the most efficacious location, and the lead is then secured by suturing the lead body to subcutaneous tissue posterior to the sacrum and attached to the output of a neurostimulator IPG. Despite the suture fixation, sacral nerve stimulation leads having a single discrete tip electrode can be dislodged from the most efficacious location due to stresses placed on the lead by an ambulatory patient. Surgical intervention can then be applied to reposition the electrode and affix the lead.

The current lead designs used for permanent implantation to provide sacral nerve stimulation through a foramen have several, e.g., four, of ring-shaped, stimulation electrodes spaced along a distal segment of the lead body adapted to be passed into or through the foramen along a selected sacral nerve. Each distal stimulation electrode is electrically coupled to the distal end of a lead conductor within the elongated lead body that extends proximally through the lead body. The proximal ends of the separately insulated lead conductors are each coupled to a ring-shaped connector element in a proximal connector element array along a proximal segment of the lead body that is adapted to be coupled with the implantable neurostimulation pulse generator, or neurostimulator IPG.

The electrode array is moved back and forth with respect to the sacral nerve while the response to stimulation pulses applied through one or more of the electrodes is determined. The IPG is programmed to deliver stimulation pulse energy to the electrode providing the optimal nerve response, and the selection of the electrodes can be changed if efficacy using a selected electrode fades over time due to dislodgement or other causes.

Electrical stimulation pulses generated by the neurostimulator IPG are applied to the sacral nerve through the selected one or more of the stimulation electrodes in either a unipolar or bipolar stimulation mode. In one unipolar stimulation mode, the stimulation pulses are delivered between a selected active one of the stimulation electrodes and the electrically conductive, exposed surface of the neurostimulator IPG housing or can that provides a remote, indifferent, or return electrode. In this case, efficacy of stimulation between each stimulation electrode and the neurostimulator IPG can electrode is tested, and the most efficacious combination is selected for use. In a further unipolar stimulation mode, two or more of the stimulation electrodes are electrically coupled together providing stimulation between the coupled together stimulation electrodes and the return electrode.

In a bipolar stimulation mode, one of the distal stimulation electrodes is selected as the indifferent or return electrode. Localized electrical stimulation of the sacral nerve is effected between the active stimulation electrode or electrodes and the indifferent stimulation electrode.

A issue associated with implantation of permanent and temporary neurostimulation leads involves placing and maintaining an electrode, such as the discrete ring-shaped electrode or electrodes, in casual contact, that is in location where slight contact of the electrode with the sacral nerve may occur or in close proximity to the sacral nerve to provide adequate stimulation of the sacral nerve, while allowing for some axial movement of the lead body.

In some examples, physicians spend a great deal of time with the patient under a general anesthetic placing the leads due to making an incision exposing the foramen and due to the difficulty in optimally positioning the small size stimulation electrodes relative to the sacral nerve. In other examples, an incision is made in the skin and a needle and guide are placed into the foramen. The patient is exposed to dangers associated with extended periods of time under a general anesthetic in order to get adequate placement. Movement of the lead, whether over time from suture release or during implantation during suture sleeve installation, is to be avoided. Also, unintended movement of any object positioned proximate a nerve may cause unintended nerve damage. Moreover, reliable stimulation of a nerve entails consistent nerve response to the electrical stimulation that, in turn, entails consistent presence of the stimulation electrode proximate the sacral nerve. But, too close or tight a contact of the electrode with the sacral nerve can also cause inflammation or injury to the nerve diminishing efficacy and possibly causing patient discomfort.

Once the optimal electrode position is attained, the lead body is fixed to retard lead migration and dislodgement of the electrodes from the optimal position employing sutures or a sacral lead fixation mechanism. It is, however, desirable to avoid use of complex fixation mechanisms.

Once fixation is completed, the proximal lead body is typically bent at about ninety degrees and tunneled subcutaneously to a remote site where its proximal connector elements are coupled to the neurostimulator IPG which is then implanted at the remote site. In this process some axial and lateral dislodgement of the stimulation electrodes can also occur.

It is generally desirable to minimize surgical trauma to the patient through surgical exposure of the tissue and sacrum. It is preferred to employ a minimally invasive, percutaneous approach in a path extending from the skin to the foramen that the neurostimulation lead is extended through.

One such percutaneous approach for implantation includes a temporary neurostimulation lead that extends through the patient's skin and is attached to an external pulse generator. Typically, the external pulse generator and exposed portion of the lead body are taped to the skin to inhibit axial movement of the lead body. When a stimulation time period ends, the lead is removed through the skin by application of traction to the exposed lead body, and the incision is closed. The neurostimulation lead bodies are formed with surface treatment or roughening in a portion proximal to the neurostimulation electrode expected to extend from the foramen to the patient's skin that is intended to increase the resistance to unintended axial dislodgement of the lead body to stabilize the electrode. A length of the lead body is formed with indentations or spiral ridges or treated to have a macroscopic roughening.

A number of configurations of implantable medical electrical leads other than neurostimulation leads employ fixation mechanisms to maintain a stimulation electrode in relation to a body organ or tissue. Cardiac pacing leads are commonly provided with passive fixation mechanisms that non-invasively engage heart tissue in a heart chamber or cardiac blood vessel or active fixation mechanisms that invasively extend into the myocardium from the endocardium or epicardium. Endocardial pacing leads having pliant tines that provide passive fixation within interstices of trabeculae in the right ventricle and atrial appendage are well known. Such tined leads typically employ three or four tines that extend outwardly and proximally from a band proximal to a distal tip pace/sense electrode and that catch in natural trabecular interstices when the distal tip electrode is advanced into the atrial appendage or the ventricular apex. Certain spinal cord stimulation leads have been proposed employing tines and/or vanes as stand-offs to urge the stimulation electrode in the epidural space toward the spinal cord and to stabilize the stimulation electrode in the epidural space, In an example directed to atrial tined leads, longitudinally extending rows of elongated tines were provided within a 270 degree arc extending away from a distal tip electrode canted in the remaining ninety degree section. The multiple rows of tines were intended to lodge in the trabecular interstices and force the canted tip against the atrial endocardial wall. It was found in practice, however, that the canted tip is unnecessary and that only three, much shorter, tines in the 270 degree arc or four tines spaced apart by ninety degrees in a common circumference like a ventricular tined lead, are sufficient. The rows of tines are necessarily closely spaced because of the small area of trabeculae in the right atrium, and more proximal tines simply typically do not engage anything and make it difficult to lodge any of the tines in the interstitial spaces.

SUMMARY

To summarize the current techniques of implantable neurostimulation for sacral nerve therapy, a small lead body is placed along the trajectory of a sacral nerve. Efficacy is often linked to the ability to place and maintain the lead in a proper position proximate the sacral nerve. The closer the lead is to the nerve, the more likely that stimulation of the lead will cause nerve activation and achieve therapy efficacy. Nerve trajectory can vary from patient to patient, and lead placement can be a difficult process for implanters. This difficulty may preclude some clinicians from performing the implant, which can affect the number of patients who have access to such procedures.

The present disclosure is directed to an example of a simpler therapy delivery that is less dependent on nerve trajectory, which could expand the number of clinicians able to provide the procedure and create more access to therapy for patients. Further, the simpler procedure can reduce time a patient may spend under anesthesia and provide for a more repeatable procedure. The medical lead of the present disclosure provides therapy to the sacral nerve in the sacral foramen. The medical lead can fill the foramen such that the stimulation of the lead captures the nerve exit location in the foramen and simplify the implant. The medical lead can include a mesh or spring electrode configured like a stent, a lead capable of being coiled in the foramen that is coiled until the foramen is filled, a tack or plug type shape to fit within the foramen, a balloon type device that is placed similar to the lead when the foramen is filled to touch the bony borders, and an electrode that creates a stimulation field that encompasses the foramina.

In such examples, the fixation may vary. For instance, the medical lead may not be configured for additional fixation or fixation mechanisms if the foramen is filled in a manner to prevent or reduce the likelihood of migration. Such examples can include the coiled lead, the stent, a spring. The medical leads can include caps on one or both sides of the foramen to retain the medical lead within the foramen. Additionally, some examples can be attached to the sacrum via such mechanisms as a screw.

In one example, the present disclosure includes an implantable medical lead. The implantable medical lead includes a lead body having a distal portion. A fixation mechanism is coupled to the distal portion. An electrode array is mechanically coupled to the fixation mechanism. In one example, the electrode array is directly coupled to the fixation mechanism. The electrode array is electrically coupled to the lead body and configured to generate a stimulation field. The fixation mechanism is configured to anchor the implantable medical lead to a sacrum and effect the stimulation field in a foramen of the sacrum. In one example, the fixation mechanism is an expandable device such as a stent that is mechanically coupled to the distal portion of the lead body. The expandable device is configured to urge against sacrum inside the foramen to anchor the implantable medical lead to the sacrum. In one example, the stent is disposed within the foramen and, in some examples, may include features that extend from the foramen. The electrode array in this example is mechanically disposed on the expandable device and electrically coupled to the lead body.

In another example, the present disclosure includes an implantable medical system having an implantable lead and a neurostimulator. The implantable medical lead includes a lead body having a distal portion. A fixation mechanism is coupled to the distal portion. An electrode array is mechanically coupled to the fixation mechanism and is electrically coupled to the lead body and configured to generate a stimulation field. The fixation mechanism is configured to anchor the implantable medical lead to a sacrum and effect the stimulation field in a foramen of the sacrum. The implantable lead is electrically coupled to the neurostimulator via a wireless receiver coupled to the lead body or via a wired connection to the neurostimulator.

In one example, the present disclosure includes an implantable medical lead. The implantable medical lead includes a lead body having a distal portion. A stent is coupled to the distal portion. An electrode array is coupled to the stent. The electrode array is electrically coupled to the lead body and configured to generate a stimulation field. The stent is configured to anchor the implantable medical lead to a sacrum and effect the stimulation field in a foramen of the sacrum. For example, the stent is configured to maintain the electrode array in the foramen.

The features of the implantable medical systems of the present disclosure are described with reference to sacral neuromodulation and implantable medical leads for use with sacral neuromodulation for illustration only. The implantable medical systems and implantable medical leads of the present disclosure can be configured and applied to as well as useful for other purposes, and other purposes can include other locations of a patient.

DETAILED DESCRIPTION

Aspects of the present disclosure provide for implantable medical devices, methods of manufacturing such implantable medical devices, and implantable medical device systems including such implantable medical devices.

Figure 1:
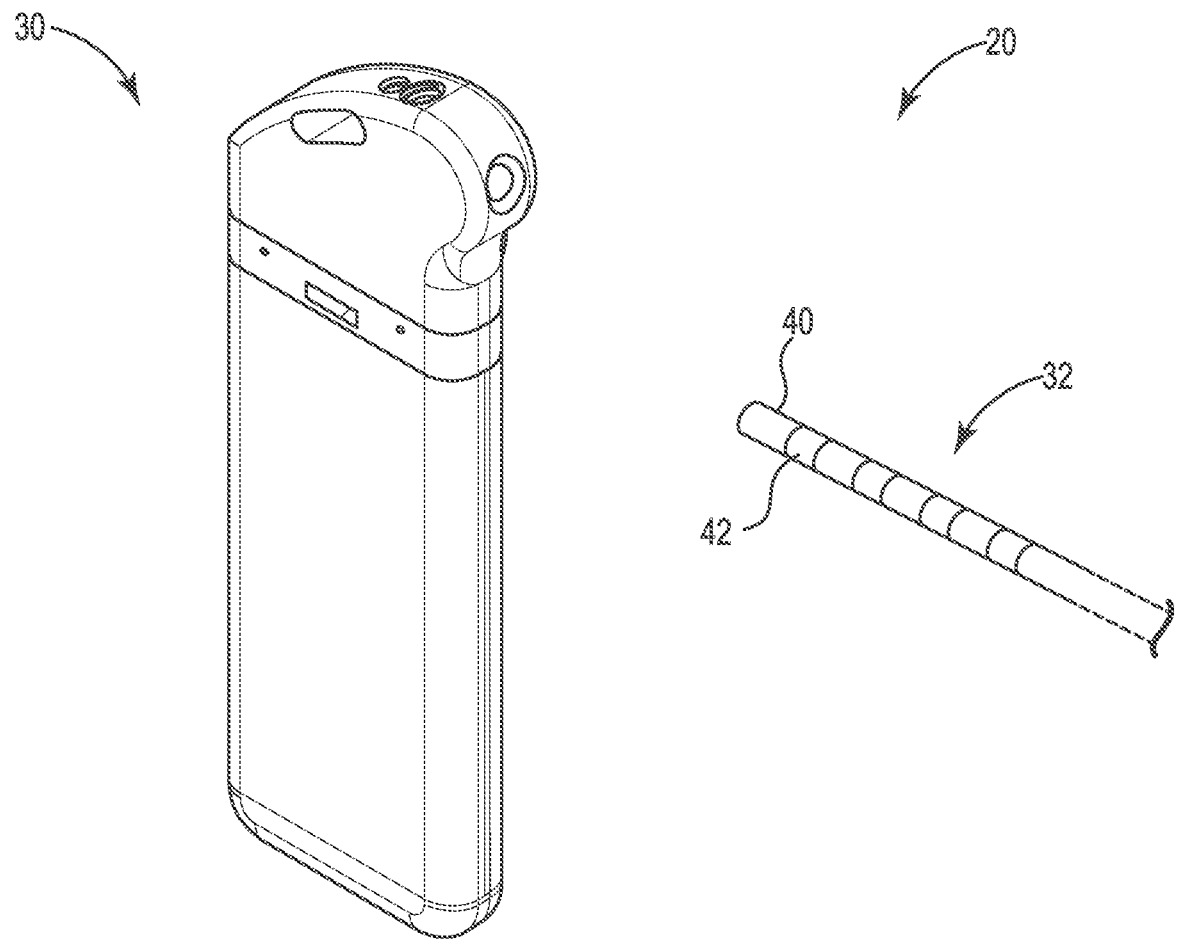
FIG. 1 is a perspective view illustrating an example implantable medical system.

FIG. 1 illustrates an implantable medical device system 20. System 20 includes an implantable medical device (IMD) 30 and an implantable medical lead 32. In general terms, the implantable medical device 30 may be of various types, such as a device for producing electrical stimulation or for sensing physiological signals for various medical applications such as neurological or cardiac therapy. The implantable medical lead 32 includes a proximal end 40 of a lead body in which a series of electrical contacts 42 are located. Each electrical contact 42 has a corresponding conductor within the lead body that extends to a distal end (not shown) where a series of electrodes are present. During use, the proximal end 40 is inserted into the implantable medical device, establishing electrical interface between the electrical contacts 42 of the implantable medical lead 32 and electrical connectors carried by the implantable medical device 30. Stimulation signals generated by the implantable medical device 30 are delivered to the distal end of the implantable medical lead 32 and to targeted tissue and/or signals sensed by the distal end of the implantable medical lead 32 at the targeted tissue are delivered to the implantable medical device 30. The systems of the present disclosure can optionally include one or more additional components, such as one or more handset programmers configured and programmed to wirelessly interface with the implantable medical device 30.

In some examples, the system 20 and the implantable medical device 30 is configured to be useful or appropriate for providing stimulation therapy to a patient, and in particular sacral neuromodulation. In some examples, the system 20 can be described as an implantable programmable neuromodulation system that delivers electrical stimulation to the sacral nerve. Sacral neuromodulation therapy provided by the system 20 can be indicated for the management of the chronic intractable functional disorders of the pelvis and lower urinary or intestinal tract including overactive bladder, fecal incontinence, and nonobstructive urinary retention.

Sacral neuromodulation creates an electrical field near the sacral nerve to modulate the neural activity that influences the behavior of the pelvic floor, lower urinary tract, urinary and anal sphincters, and colon. The system 20 is configured to use current controlled stimulation to generate an electric field to modulate the sacral nerve. Electrical stimulation is delivered using metal electrodes provided with the implantable medical lead 32, which carry current in the form of electrons, to biological tissue, which carries current in the form of ions. An interface between the electrode and the tissue includes non-linear impedance that can be a function of the voltage across that interface. During current-controlled stimulation, an amount of current is regulated. The voltage is changed according to the actual value of impedance, such that changes in impedance will not affect the total amount of current delivered to the tissue. Current controlled waveforms can ensure that the electric field in the tissue is independent of electrode polarization or the voltage drop across the electrode-electrolyte interface. Alternatively, the systems of the present disclosure can be configured or programmed to use voltage-controlled stimulation.

Figure 2:
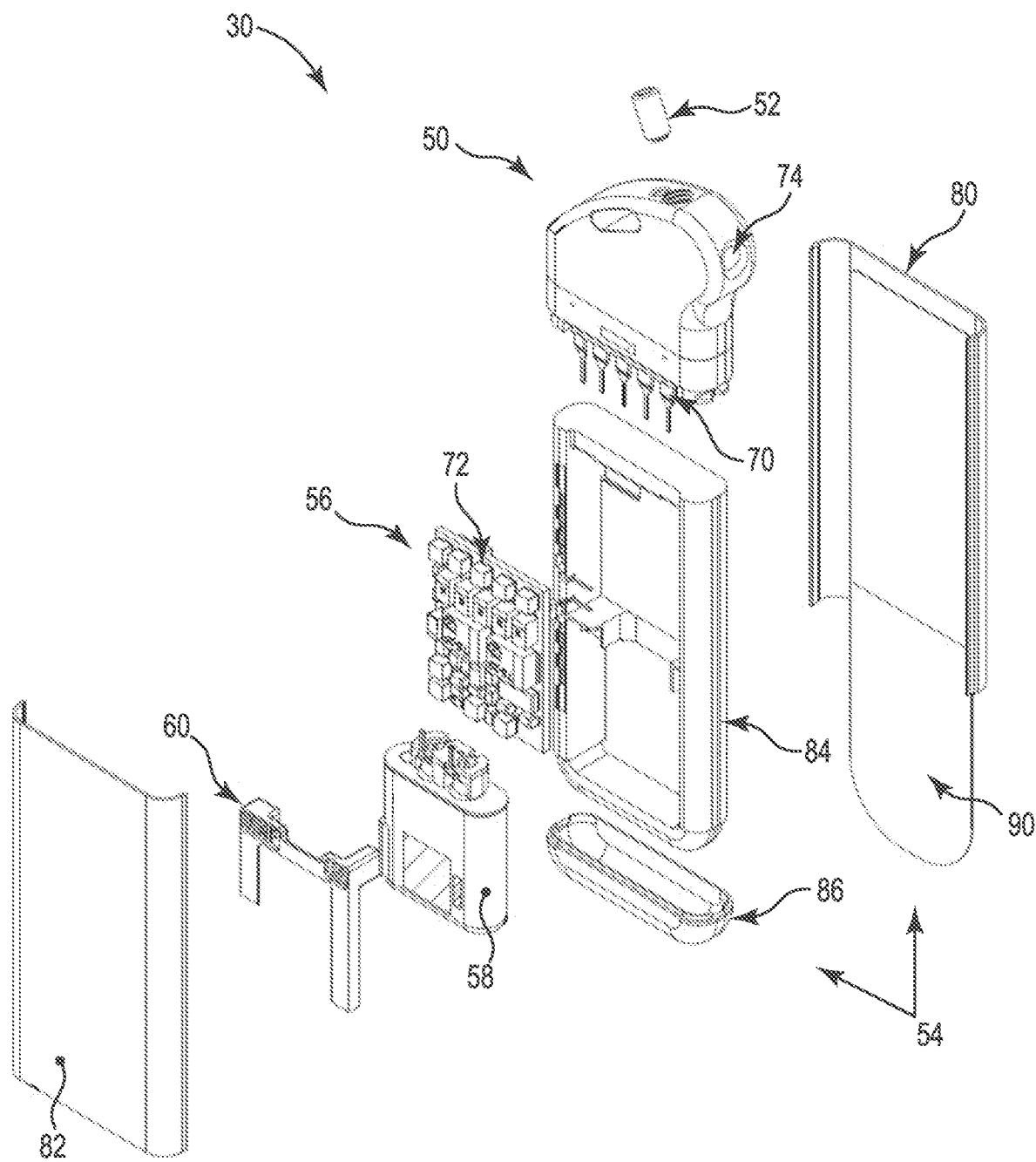
FIG. 2 is an exploded perspective view illustrating an implantable medical device useful with the system of FIG. 1.

FIG. 2 illustrates an example of the implantable medical device 30 appropriate, for example, for generating the sacral neuromodulation therapy stimulation signals. The implantable medical device 30 can be configured to provide a small form factor, e.g., a volume on the order of approximately 3 cubic centimeters in some non-limiting embodiments, while generating desired stimulation signals over an extended lifetime. The implantable medical device 30 can serve as the power source of the sacral neuromodulation therapy described above in some embodiments. The smaller form factor or size as compared to conventional stimulation-type implantable medical devices can allow for a smaller implant location incision and smaller subcutaneous pocket, which may result in a more discreet implant. In some embodiments, the implantable medical device 30 incorporates various features described below that facilitate the small form factor size while providing desired performance attributes, such as remotely programmable stimulation signals or electrical pulses at therapy levels of interest, magnetic resonance imaging (MM) compatibility, and remote charging.

In some embodiments, the implantable medical device 30 includes or defines a connector enclosure assembly 50, a set screw 52, a main enclosure assembly or can 54, electrical circuitry 56, a battery 58, and an optional desiccant assembly 60. Details on the various components are provided below. In general terms, the electrical circuitry 56, the battery 58 and the desiccant assembly 60 are maintained within the can 54. The battery 58 is electrically coupled to the electrical circuitry 56. The connector enclosure assembly 50 is assembled to the can 54, and includes one or more conductor fingers 70 that are electrically connected to individual circuitry components, and in particular contact pads 72, of the electrical circuitry 56. With this construction, electrical signals generated by the electrical circuitry 56 are delivered to the connector enclosure assembly 50 via the conductor fingers 70. The connector enclosure assembly 50 further forms or defines an entryway 74 sized to receive the proximal end 40 of the implantable medical lead 32. Electrical connectors provided with the connector enclosure assembly 50 interface with the electrical contacts 42 and are electrically connected to respective ones of the conductor fingers 70, thereby connecting the electrical circuitry 56 with implantable medical lead 32. The set screw 52 provides an electrical ground between the implantable medical lead 32 as inserted into the entryway 72 and the can 54.

In an alternate example, the medical device and implantable medical lead are configured for wireless signal transmission. For example, the medical device can include a transmitter and receiver electrically coupled to a transmitter and receiver on the implantable medical lead to provide or exchange signals between the medical device and the implantable medical lead.

The can 54 can assume various forms appropriate for maintaining the electrical circuitry 56 and the battery 58, as well as for assembly with the connector enclosure assembly 50. In some embodiments, the can 54 includes opposing shield bodies 80, 82, an insulator cup 84 and an end cap 86. The shield bodies 80, 82 can be formed of a surgically safe, robust material, e.g., titanium, such as a titanium alloy 6A1-4V ELI alloy per ASTM F136, and collectively generate a sleeve, e.g., the shield bodies 80, 82 can be secured to one another by, for example, laser seam welding applied to the interfacing edges. The sleeve, in turn, defines an open volume sized and shaped to receive the insulator cup 84. To facilitate final construction, a pressure sensitive adhesive liner 90 can be provided with the first shield body 80 that is removed prior to assembly to the insulator cup 84. A bottom opening to the sleeve collectively defined by the shield bodies 80, 82 is closed by the end cap 86. The end cap 86 and the connector enclosure assembly 50 can be assembled (e.g., welded) to the shield bodies 80, 82 to provide a hermetically sealed case.

The insulator cup 84 serves as a chassis, sized and shaped to fit snugly between the shield bodies 80, 82. The insulator cup 84 spatially secures the electrical circuitry 56 and the battery 58 via appropriately sized and shaped cavities. The insulator cup 84 can be formed of an electrically non-conductive or insulative material, such as a polymer.

The electrical circuitry 56 can include various electrical components and connections appropriate for providing, in some non-limiting embodiments, a pulse generator for therapy stimulation, e.g., a constant current stimulation engine, sensing circuitry for measuring physiological parameters, telemetry for communication with external devices (e.g., inductive telemetry at 175 KHz), memory, and a recharge circuit in some non-limiting embodiments. For example, the electrical circuitry 56 can deliver stimulation signals to the contact pads 72, and can process or act upon sensed signals received at the contact pads 72. The electrical circuitry 56 optionally provides various stimulation signal parameters, for example current controlled amplitude with a resolution of 0.1 mA steps, an upper limit of 12.5 mA, and a lower limit of 0.0 mA; a rate of 3-130 kHz; pulse width increments of 10 µs steps with a maximum of 450 µs and a minimum of 20 µs.

The battery 58 can assume various forms appropriate for generating desired stimulation signals, and in some embodiments is a rechargeable battery. For example, the battery 58 can incorporate lithium ion (Li+) chemistry, although other battery constructions known in the art are also acceptable.

The desiccant assembly 60 is sized and shaped for mounting within the can 54, and provides or carries an appropriate desiccant material to promote a dry environment within the can 54.

The connector enclosure assembly 50 can be mounted to the can 54 in a hermetically sealed fashion. The conductor fingers 70 and the ground conductor 124 are arranged to extend to a corresponding one of the contact pads 72, and are welded, e.g., pressure gas welding. The desiccant assembly 60 can be placed into the can 54 following the welding process, or otherwise delayed until a remaining step is to add the second shield body 82. In this manner, the desiccant is exposed to the ambient conditions for only a short time prior to the interior of the can 54 being isolated from the exterior. This can preserve the effectiveness of the desiccant.

Figure 3:
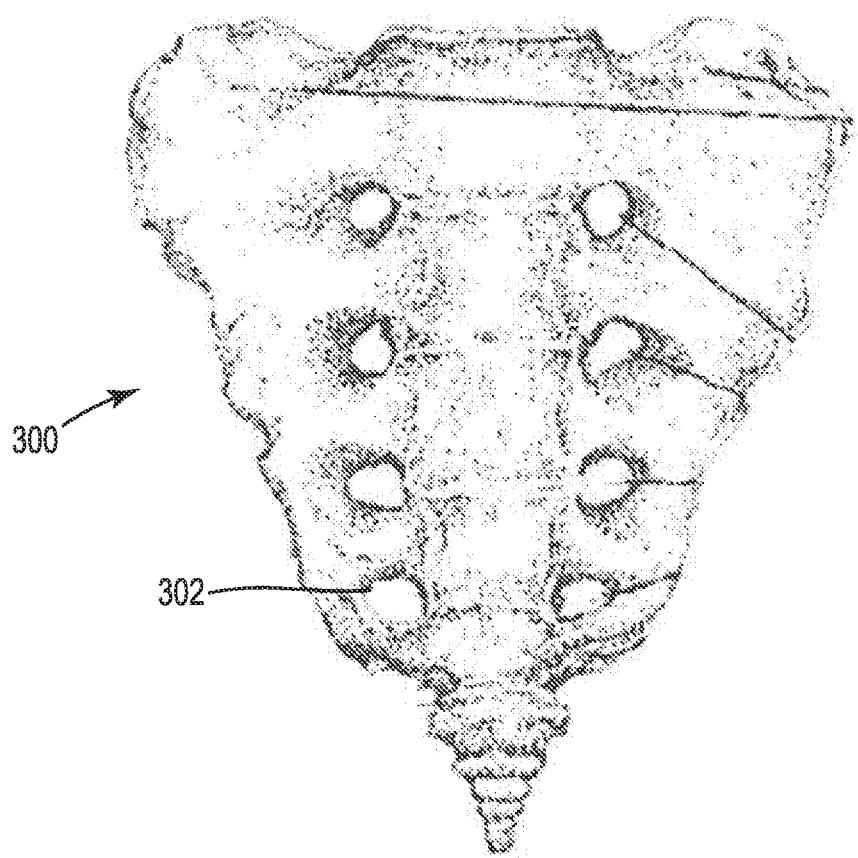
FIG. 3 is a schematic front view illustrating an example sacrum that include foramina through which sacral nerves may extend.

FIG. 3 illustrates an example sacrum 300. The sacrum 300 includes a plurality of foramina, such as foramen 302. The pelvic surface of the sacrum (illustrated) is concave from the top, and curved slightly from side to side (a convex dorsal surface is opposite the pelvic surface and not shown). Its middle part is crossed by four transverse ridges, which correspond to the original planes of separation between the five sacral vertebrae. The body of the first segment is large and has the form of a lumbar vertebra; the bodies of the next bones get progressively smaller, are flattened from the back, and curved to shape themselves to the sacrum, being concave in front and convex behind. At each end of the transverse ridges, are the four anterior sacral foramina, diminishing in size in line with the smaller vertebral bodies. The foramina give exit to the anterior divisions of the sacral nerves and entrance to the lateral sacral arteries. Each part at the sides of the foramina is traversed by four broad, shallow grooves, which lodge the anterior divisions of the sacral nerves.

There are five paired sacral nerves, half of them arising through the sacrum on the left side and the other half on the right side. Each nerve emerges in two divisions: one division through the anterior sacral foramina and the other division through the posterior sacral foramina. The nerves divide into branches and the branches from different nerves join with one another, some of them also joining with lumbar or coccygeal nerve branches. These anastomoses of nerves form the sacral plexus and the lumbosacral plexus. The branches of these plexus give rise to nerves that supply much of the hip, thigh, leg and foot. The sacral nerves have both afferent and efferent fibers and are responsible for part of the sensory perception and the movements of the lower extremities of the human body. From the S2, S3 and S4 arise the pudendal nerve and parasympathetic fibers whose electrical potential supply the descending colon and rectum, urinary bladder and genital organs. These pathways have both afferent and efferent fibers and, this way, they are responsible for conduction of sensory information from these pelvic organs to the central nervous system (CNS) and motor impulses from the CNS to the pelvis that control the movements of these pelvic organs.

Figure 4:
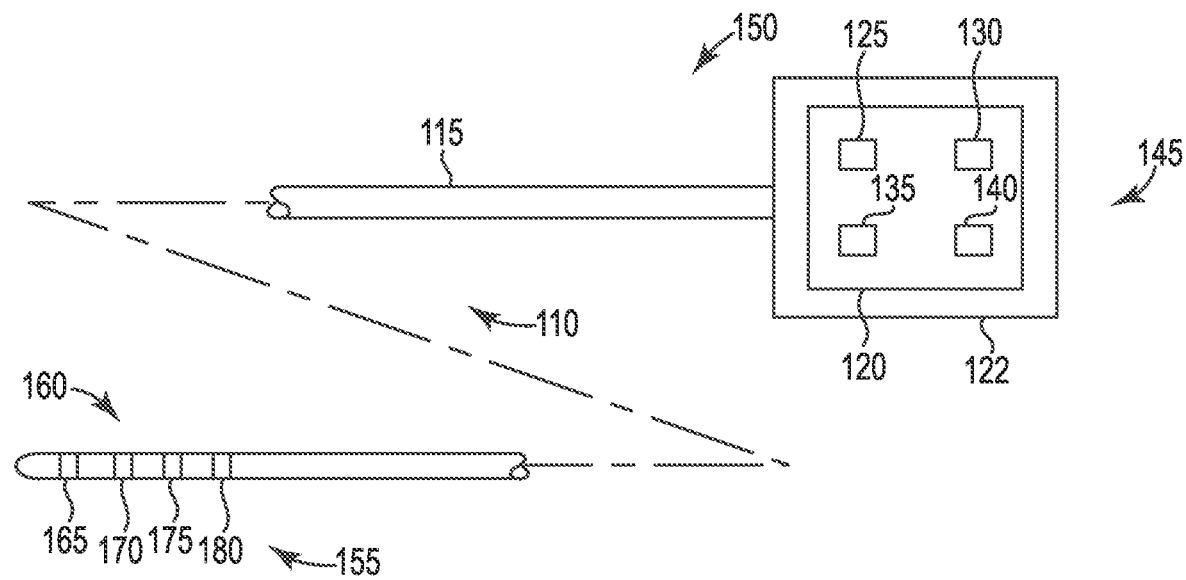
FIG. 4 is a plan view illustrating an example implantable medical lead that can be used with the implantable medical system of FIG. 1.

FIG. 4 illustrates a schematic example of an implantable medical lead 110, which can be an example of implantable medical lead 32, that may be applied to provide sacral nerve stimulation that allow for non-direct contact stimulation of the sacral nerves and comprises a lead body 115, an electrode array 120 configured to provide or receive electrical signals such as stimulation signals to the sacral nerve within the foramen, and a fixation mechanism 122 to hold the electrode array 120 within the foramen. In one example, the fixation mechanism 122 is configured to prevent or reduce the likelihood of migration of the electrode array 120. In one example, the fixation mechanism 122 can provide an anchor to the sacrum such as to the wall or surrounding structures of the foramen or the tissues proximate the sacrum.

The electrode array 120 can include one or more electrodes, such as four electrode 125, 130, 135, and 140. In the illustrated example, the electrode array 120 is disposed on a lead distal end 145. In another example, an implantable medical lead could include an electrode array with a single electrode disposed on the distal end of the lead body. Other configurations are contemplated. An outer diameter of the lead body 115 can be in the range of about 0.5 mm to about 2 mm. In one example, the electrodes 125, 130, 135 and 140 are made of a solid surface, bio-compatible material such as a pad or tube formed of platinum, platinum-iridium alloy, or stainless steel, of about 3.0 mm in length that does not degrade when electrical stimulation is delivered through. The electrode can further be separated by insulator bands.

Each stimulation electrode in the electrode array 120, such as 125, 130, 135, and 140, is electrically coupled to the distal end of a coiled wire lead conductor within the elongated lead body 115 that extends proximally through a distal portion 150 and through a proximal portion 155 of the lead body 115. The proximal ends of the separately insulated lead conductors can each be coupled to respective ring-shaped connector elements 165, 170, 175, and 180 in a proximal connector element array 160 along the proximal portion 155 of the lead body 115 adjacent the lead proximal end 185. The conductor wires can be formed of an M35N alloy and are insulated from one another within an insulating polymer sheath such as polyurethane, fluoropolymer, or silicone rubber. An example diameter of the lead body 115 is 1.3 mm but smaller diameters are also contemplated. The lead conductor wires are separately insulated by an insulation coating and are wound in a quadra-filar manner having a common winding diameter within the outer sheath. The coil formed by the coiled wire conductors defines a lead body lumen of the lead body 115. In some examples, a further inner tubular sheath could be interposed within the aligned wire coils to provide the lead body lumen.

The connector elements 165, 170, 175, and 180 are adapted to be coupled with a neurostimulator IPG, such as implantable medical device 30, additional intermediate wiring, or other stimulation device adapted to be implanted subcutaneously. An example of such an implantable pulse generator is available under the trade designation Medtronic InterStim Neurostimulator from Medtronic, Inc. Electrical stimulation pulses generated by the implantable medical device 30 are applied to the sacral nerve through one or more of the stimulation electrodes 125, 130, 135 and 140 in a unipolar or bipolar stimulation mode.

The axial lead body lumen (not shown) extends the length of the lead body 115 between a lumen proximal end opening at lead proximal end 185 and a lumen distal end opening at lead distal end 145. A straight wire attached to the handle of a guide wire or stiffening stylet can be inserted through the lead body lumen to assist in implanting the lead 110.

The fixation mechanism 122 can be formed on the lead body 115 in the distal lead portion 150 that is adapted to be implanted in the foramen to inhibit axial movement of the lead body 115 and dislodgement of the stimulation electrodes 125, 130, 135 and 140 in the example. For example, the fixation mechanism 122 can be formed on the lead body 115 in the distal portion but spaced apart from the distal tip. In one example, the fixation mechanism 122 is disposed within the electrode array 120. In another example, the fixation mechanism 122 can be disposed within and proximal to the electrode array 120. In still another example, the fixation mechanism 122 can disposed distal to the electrode array 120 such as on the lead distal end 145. In still another example, the fixation mechanism 122 can be disposed to be completely proximal to the electrode array 120. Other configurations are contemplated. Further, the fixation mechanism 122 can be applied in conjunction with another fixation mechanism such as an array of tines that include a larger outside diameter. The array of tines can be disposed proximal to the fixation mechanism 122.

Figure 7:
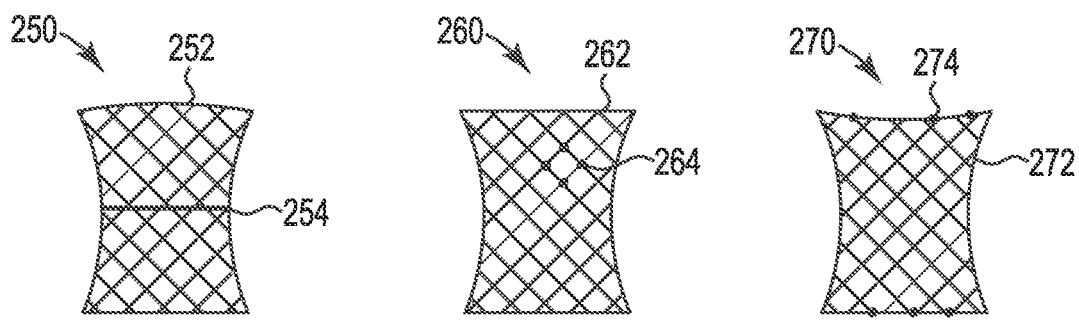
FIG. 7 is a schematic side view illustrating a plurality of example electrode arrays that can be used with an implantable medical lead and system of FIG. 1, such as the example fixation mechanisms of FIG. 6.
Figure 8:
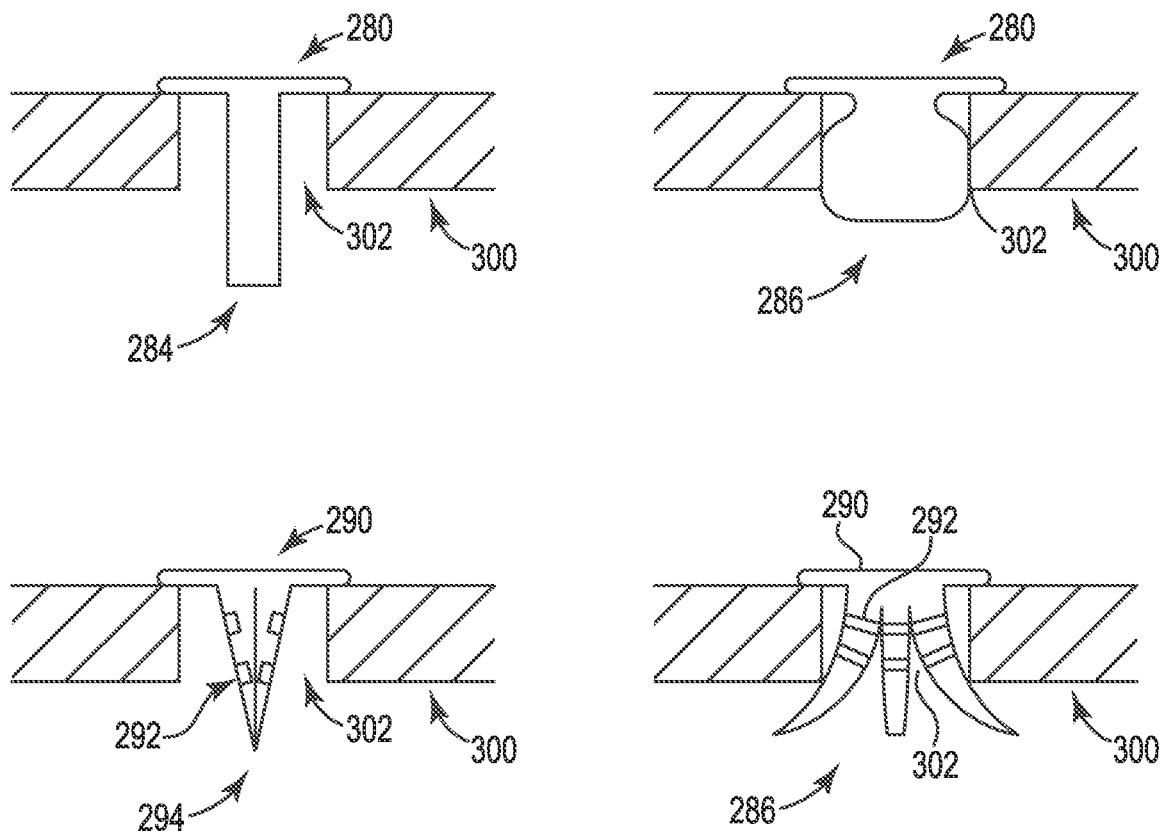
FIG. 8 is a schematic side view illustrating two fixation mechanisms configured to carry electrode arrays in accordance with the example of FIG. 4, in which the fixation mechanisms are in a undeployed state and a deployed, or expanded state. The examples are applicable to the various fixation mechanisms of the disclosure.

As illustrated and described in the disclosure, the electrodes array 120 is disposed on the fixation mechanism 122 and electrically coupled to the lead body 115. For example, the implantable medical lead 110 includes a lead body 115, a fixation mechanism 122 attached to the lead body 115, and an electrode array 120 mechanically attached to the fixation mechanism 122. The implantable medical lead 110 includes an axial direction, as indicated by the axis between the distal portion 150 and the proximal portion 155, and the fixation mechanism 122 extends along the axial direction having a fixation proximal end and a fixation distal end. The electrode array 120 is disposed entirely within the proximal end and the distal end of the fixation mechanism 122. (This example configuration is illustrated in FIGS. 7 and 8.) In one example, none of the electrodes are disposed on the lead body, and all of the electrodes are disposed on the fixation mechanism. In this implementation, for example, the fixation mechanism 122 is configured to anchor the implantable medical lead 100 to a sacrum 300 or surrounding tissue and effect the stimulation field in a foramen 302 or the dorsal or ventral exit point of the foramen of the sacrum.

Figure 5:
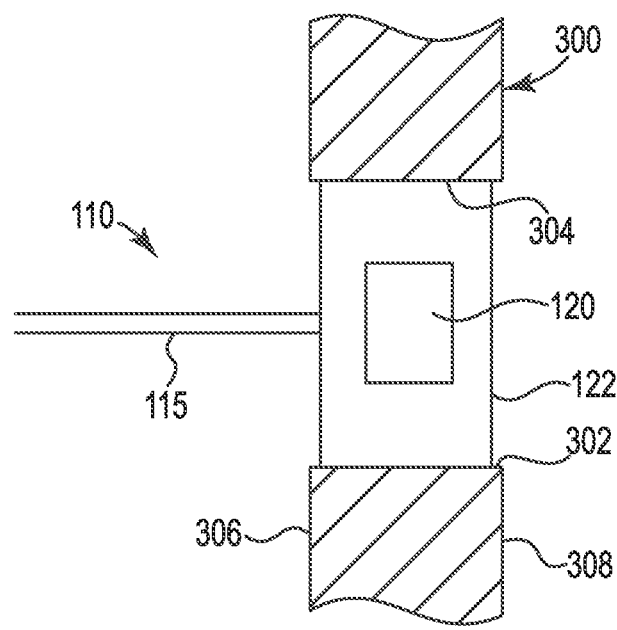
FIG. 5 is a side sectioned view illustrating the sacrum of FIG. 3 having a sacral nerve extending from a foramen, and the example implantable medical lead of FIG. 4 deployed into the foramen and configured to provide stimulation to the sacral nerve.

FIG. 5 illustrates a schematic view of the implantable medical lead 110 deployed into a sacrum, such as sacrum 300. The illustration indicates a side view of the sectioned sacrum, which includes a foramen, such as foramen 302. An example sacral nerve 304 extends from the sacrum 300 through the foramen 302. The example sacrum 300 can include a first surface 306 and an opposite second surface 308, which may correspond with one of the pelvic and dorsal or dorsal and pelvic surfaces, respectively. The fixation mechanism 122 is deployed into the foramen 302 to engage the sacrum 300 at the walls of the foramen 302 or one or both of the first and second surfaces 306, 308 to maintain the position of the electrode array 120, which provides stimulation to the sacral nerve 304 within the foramen 302. In one example, the fixation mechanism 122 is configured to maintain the position of the electrode array within the foramen 302. For instance, all of the electrodes configured to engage the sacral nerve 304 with non-direct stimulation are disposed and maintained within the foramen as defined by the walls of the sacrum. In another example, the fixation mechanism 122 is configured to maintain the stimulation field provided by the electrode array 120 within the foramen 302. For instance, all of the stimulation fields configured to engage the sacral nerve 304 and produced by the electrodes of the electrode array 120 are within the foramen. In this instance, an electrode of the electrode array may be positioned and maintained outside of the foramen 302 but produce a stimulation field that engages the sacral nerve 304 within the foramen.

In one example, the implantable medical lead 110 can be inserted into the foramen 302 in a first state, such as an undeployed state. For instance, the fixation mechanism 122 can be compressed in a first state. Once in the foramen 302, the implantable medical lead 110 can be transitioned to a second state, such as a deployed state. For instance, the electrode array 120 can be positioned into the foramen 302 or the electrode array can be positioned to provide or effect the stimulation field within the foramen 302, and the fixation mechanism 122 can be expanded to fit within the foramen 302. In the deployed state, the fixation mechanism 122 can maintain the electrode array or the stimulation field within the foramen 302.

Figure 6:
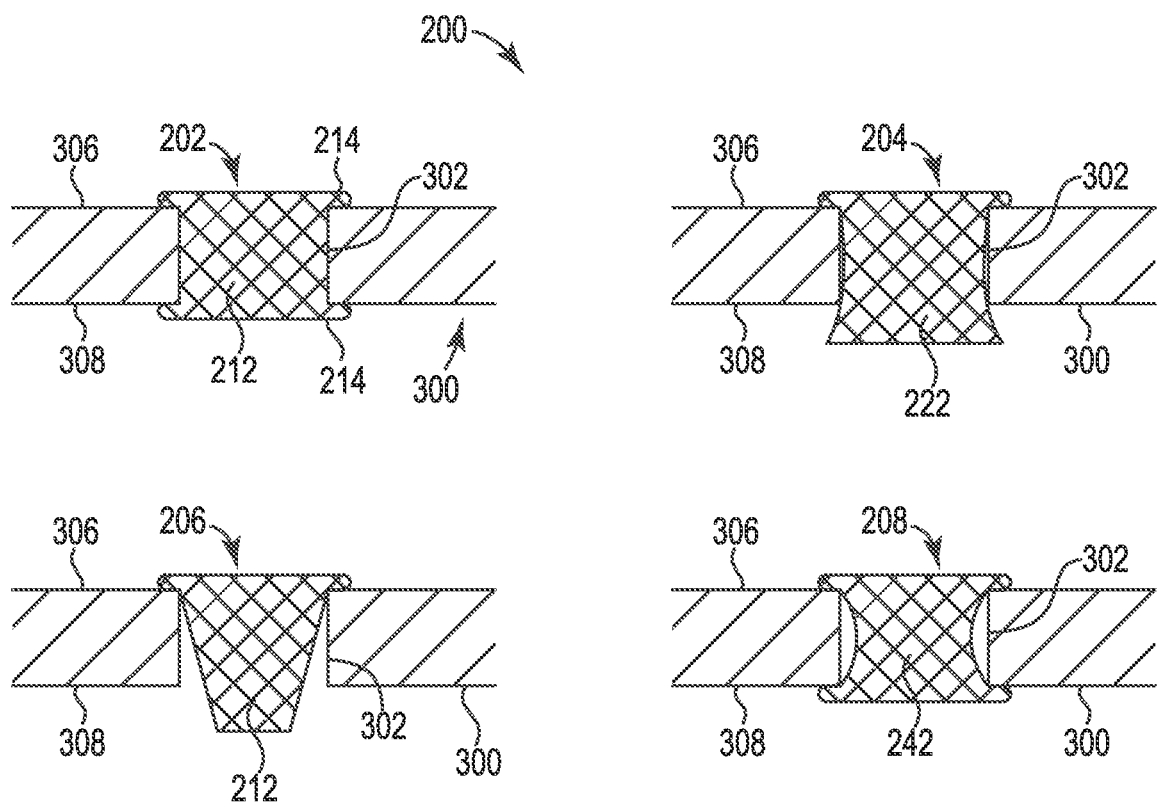
FIG. 6 is a schematic side view illustrating a plurality of example fixation mechanisms that can be used with an implantable medical lead and system of FIG. 1.

FIG. 6 illustrates a plurality of example fixation mechanisms 200, such as 202, 204, 206, 208, that may be included as fixation mechanism 122 on implantable medical lead 110. In the example, the lead body 115 is coupled to the fixation mechanism 122. In the example, the fixation mechanism 200 are stents. Stents are generally elongated devices having an oval or circular cross-section that are radially expandable to radially urge against the walls of a foramen 302, such as within sacrum 300, or another anatomical lumen, after implantation into the body lumen. In general, the stents may be an expandable or a self-expanding stent. Expandable stents generally are conveyed to the area to be treated on an expandable device. For insertion into the body, the stent is positioned in a compressed configuration on the delivery device. For example, the stent may be crimped onto a balloon that is folded or otherwise wrapped about the distal portion of a body that is part of the delivery device. After the stent is positioned within the foramen 302, it is expanded by the delivery device, causing the diameter of the stent to expand. For a self-expanding stent, commonly a sheath is retracted, allowing the stent to expand. An example stent can comprise a plurality of elongated strut portions and a plurality of flexible crown portions extending from the strut portions. The strut portions may intersect at vertices. When the stent is radially expanded the flexible crown portions assume a diameter recoil prevention position. Metallic stents can comprise a variety of biocompatible metals including stainless steel, titanium, gold, nickel/titanium alloys, such as nitinol, platinum, and platinum-tungsten alloys. These metallic materials are sufficiently flexible to allow the stent to be compressed and expanded, but also provide sufficient radial strength to maintain the stent in the expanded configuration and apply adequate force to the walls of the foramen to hold the stent in place. Polymeric stents may be constructed from biostable polymers appropriate for the stents that can include polyethylene, polypropylene, polymethyl methacrylate, polyesters, polyamides, polyurethanes, polytetrafluoroethylene (PTFE), polyvinyl alcohol, and other suitable polymers. These polymers may be used alone or in various combinations to give the stent unique properties such as to form biostable stents with a biodegradable or bioerodable coating that may reduce inflammation, control tissue ingrowth, and additionally, release a drug.

As illustrated, the fixation mechanisms include an elongate side that is configured to extend along an axis of the foramen, which also can be configured to extend along the axis of the lead body of the implantable medical lead. The elongate side includes an elongate length. The fixation mechanisms also include a radial dimension such as a diameter or a width. The fixation mechanisms are configured to be mechanically attached to a distal portion of the implantable medical lead.

In the example, fixation mechanism 202, illustrated in a side view, is a cylindrical stent having a generally cylindrical body 212. The cylindrical body 212 includes an elongate side that is configured to extend along an axis of the foramen 302 and a generally circular or oval cross-section that is configured to radially expand to engage the sacrum 300 or at least include portions that engage the sacrum 300 at the walls of the foramen in a deployed or expanded state. The elongate side may be long enough to extend through the foramen or may be short enough to be deployed entirely within the foramen 302.

In the example, fixation mechanism 202 includes optional caps 214 on both first and second ends of the body. The caps are larger in diameter than the foramen such that the caps can engage the respective first and second surfaces 306, 308 of the sacrum 300 for further fixation. Examples 204, 206, and 208 each include one or two caps, but such caps are optional. A stent body may be provided with zero or more caps.

In the example, fixation mechanism 204, illustrated in a side view, is a stent having a generally tapered body 222. The tapered body 222 includes an elongate side that is configured to extend along an axis of the foramen 302 and a generally circular or oval cross-section in which one end of the body 222 includes a diameter of the cross-section that is generally larger than the size or diameter of the foramen. The other end of the body 222 may include a diameter of the cross-section that is at least as large or smaller than the size of the foramen. The body 222 is configured to radially expand to engage the sacrum 300 or at least include portions that engage the sacrum 300 at the walls of the foramen in a deployed or expanded state. The fixation mechanism 204 is illustrated with an option cap.

In the example, fixation mechanism 206, illustrated in a side view, is a stent having a generally tapered body 232. The tapered body 232 includes an elongate side that is configured to extend along an axis of the foramen 302 and a generally circular or oval cross-section in which one end of the body 232 includes a diameter of the cross-section that is generally smaller than the size or diameter of the foramen. The other end of the body 232 may include a diameter of the cross-section that is at least as large as the size of the foramen. The body 232 is configured to radially expand to engage the sacrum 300 or at least include portions that engage the sacrum 300 at the walls of the foramen in a deployed or expanded state. The elongate side may be long enough to extend through the foramen or may be short enough to be deployed entirely within the foramen 302. The fixation mechanism 206 is illustrated with an option cap.

In the example, fixation mechanism 208, illustrated in a side view, is a stent having a generally hour-glass shaped body 242. The body 242 includes an elongate side that is configured to extend along an axis of the foramen 302 and a generally circular or oval cross-section that is in which both ends of the body 242 includes a diameter of the circular cross-section that is generally larger than the size or diameter of the foramen and the medial portion of the body 242. The body 242 is configured to radially expand to engage the sacrum 300 or at least include portions that engage the sacrum 300 at the walls of the foramen in a deployed or expanded state. The elongate side may be long enough to extend through the foramen or may be short enough to be deployed entirely within the foramen 302. The fixation mechanism 204 is illustrated with a pair of optional caps.

FIG. 7 illustrates a plurality of possible electrodes for an electrode array disposed on a fixation mechanism, such as fixation mechanism 200, illustrated in a side view. Implantable medical lead 250 includes fixation mechanism configured as a stent 252 or similar device and an electrode array comprising a ring electrode disposed around the body of the stent or similar device. In one example, the electrode array 254 can include a plurality of spaced-apart ring electrodes along the elongate side or length of the electrode body, or other electrodes. The ring can be divided into segments, such as quarters or quadrants, to better direct the field or current of interest to where, such as which quadrant, the nerve lies. Implantable lead 260 includes a fixation mechanism configured as a stent 262 or similar device and can include an electrode array 264 having a plurality of pad electrodes disposed on the body of the stent or similar device, such as on the joints of the intersecting struts. The electrode array 264 can extend along the length of the body, or a portion of the length of the body, and along an arc of the circumference of the body or along the entire circumference of the body. Implantable lead 270 includes a fixation mechanism configured as a stent 272 or similar device and can include an electrode array 274 having a plurality of pad electrodes disposed on the ends of the body. The electrode array 274 can extend along the length an arc of the circumference of the end or along the entire circumference of the end. In one example, the number of electrodes in the electrode array 274 can include more than four electrodes. For instance, the more than one electrode may correspond with a single stimulation signal. When deployed, the closest electrode corresponding with the single stimulation signal may be activated, and the remaining electrode or electrodes that also correspond with the stimulation signal may be rendered dormant.

In an implantable medical lead, as indicated, the electrodes in the electrode array are mechanically attached to the fixation mechanism and are electrically coupled to lead body and the connector elements in the connector array of the proximal portion of the lead body.

FIG. 8 illustrates two schematic examples of a fixation mechanism in an undeployed position transitioned to a deployed position. In one example, fixation mechanism 280 is configured as a device having an expandable section and an optional base, which may correspond with a cap. An electrode array (not shown) can be disposed on the base, the expandable section, or both. In the undeployed position 284, the expandable section is in an unexpanded, first position to provide a relatively thin profile that may be inserted into the foramen. In the example, the base is configured to be larger than the size of the foramen, and is urged against a first or second surface of the sacrum. In the deployed position 286, the expandable section is expanded inside the foramen, and the expandable section and base, if included, prevent movement of the fixation mechanism 280 along an axis of the foramen. If the expandable section is spread wide enough to engage the walls of the foramen or the surface of the sacrum opposite the base, the expandable section and base should prevent movement of the fixation mechanism 280 around the axis of the foramen. The fixation mechanism 280 can be urged between two opposing forces along the axis of the foramen with a deployment device to spread the expandable section. Further, the fixation mechanism may remain in the unexpanded position and still engage the foramen to remain in place.

In another example, fixation mechanism 290 is configured as a tack-like device having a shoulder and a plurality of arms extending from the shoulder. An electrode array 292 can be disposed on the arms of the tack. In the undeployed position 294, the arms of the tack are together and provide a relatively thin profile that may be inserted into the foramen. In the example, the shoulder is configured to be larger than the size of the foramen, and is urged against a first or second surface of the sacrum. In the deployed position 296, the arms of the tack are spread apart inside the foramen, and the arms and shoulder prevent movement of the fixation mechanism 290 along an axis of the foramen. If the arms are spread wide enough to engage the walls of the foramen or the surface of the sacrum opposite the shoulder, the arms and should prevent movement of the fixation mechanism 290 around the axis of the foramen. The fixation mechanism 290 can be urged between two opposing forces along the axis of the foramen with a deployment device to spread the arms.

As illustrated, the fixation mechanisms include an elongate side that is configured to extend along an axis of the foramen, which also can be configured to extend along the axis of the lead body of the implantable medical lead. The elongate side includes an elongate length. The fixation mechanisms also include a radial dimension such as a diameter or a width. The fixation mechanisms are configured to be mechanically attached to a distal portion of the implantable medical lead. In an implantable medical lead, as indicated, the electrodes in the electrode array are mechanically attached to the fixation mechanism and are electrically coupled to lead body and the connector elements in the connector array of the proximal portion of the lead body.

Figure 9:
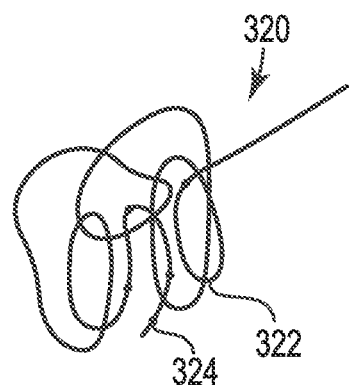
FIG. 9 is a schematic side view illustrating an implantable medical lead having another example of a fixation mechanism and electrode array configured in accordance with the example of FIG. 4.

FIG. 9 illustrates still another example of an implantable lead, such as lead 320 having a fixation mechanism 322 configured as an expandable coil and an electrode array 324 having a plurality of spaced-apart electrodes disposed along the coil. The coil configured to be inserted into the foramen in an undeployed state and expanded to fit against the walls of the foramen or may be urged against the opposing surfaces 306 of the sacrum 300. In the deployed state, as illustrated, the electrodes are disposed within the foramen.

Although the present disclosure has been described with reference to preferred embodiments, workers skilled in the art will recognize that changes can be made in form and detail without departing from the spirit and scope of the present disclosure.

What is claimed is:

1. An implantable medical system comprising:
   an implantable medical lead comprising:
   a lead body having a distal portion;
   a fixation mechanism coupled to the distal portion, the fixation mechanism including an end portion and an expandable portion; and
   an electrode array disposed on the expandable portion of the fixation mechanism, electrically coupled to the lead body, and configured to generate a stimulation field;
   wherein the fixation mechanism is configured to anchor the implantable medical lead to a sacrum or surrounding tissue and effect the stimulation field in a foramen or the dorsal or ventral exit point of the foramen of the sacrum,
   wherein the expandable portion is configured to radially urge against a first surface within the foramen of the sacrum, and
   wherein the end portion defines a diameter larger than the expandable portion and is configured to engage a second surface of the sacrum different than the first surface.

2. The system of claim 1 wherein the fixation mechanism is configured to anchor the implantable medical lead to the sacrum within the foramen.

3. The system of claim 1 wherein the fixation mechanism is configured to dispose the electrode array within the foramen.

4. The system of claim 1 including a neurostimulator operably coupled to the implantable medical lead.

5. The system of claim 4 wherein the electrode array is electrically coupled to a wireless receiver in electrical communication with the neurostimulator.

6. The system of claim 4 wherein the implantable medical lead includes a proximal end having a proximal array electrically coupled to the electrode array and mechanically and electrically coupled to the neurostimulator.

7. The system of claim 4 wherein the neurostimulator is an implantable medical device.

8. The system of claim 1 wherein the electrode array includes four electrodes.

9. An implantable medical lead comprising:
   a lead body having a distal portion;
   and
   a fixation mechanism mechanically coupled to the distal portion, the fixation mechanism including an end portion and an expandable portion; and
   an electrode array directly mechanically coupled to the expandable portion of the fixation mechanism and electrically coupled to the lead body, the electrode array configured to generate a stimulation field;
   wherein the fixation mechanism configured to anchor the implantable medical lead to a sacrum and effect the stimulation field in a foramen of the sacrum,
   wherein the expandable portion is configured to radially urge against a first surface within the foramen of the sacrum, and
   wherein the end portion defines a diameter larger than the expandable portion and is configured to engage a second surface of the sacrum different than the first surface.

10. The lead of claim 9 wherein the fixation mechanism is configured to anchor the implantable medical lead to the sacrum within the foramen.

11. The lead of claim 9 wherein the fixation mechanism is configured to dispose the electrode array within the foramen.

12. The lead of claim 9 wherein the electrode array is electrically coupled to a wireless receiver.

13. The lead of claim 9 wherein the lead body includes a proximal end having a proximal array electrically coupled to the electrode.

14. The lead of claim 9 wherein the electrode array includes four electrodes.

15. The lead of claim 9 wherein the expandable portion includes a stent.

16. An implantable medical lead comprising:
   a lead body having a distal portion;
   a stent coupled to the distal portion, the stent including an end portion and an expandable portion and configured to anchor the implantable medical lead to a sacrum; and
   an electrode array directly mechanically coupled to the stent and electrically coupled to the lead body, the electrode array configured to generate a stimulation field and effect the stimulation field in a foramen of the sacrum,
   wherein the expandable portion is configured to radially urge against a first surface within the foramen of the sacrum, and
   wherein the end portion defines a diameter larger than the expandable portion and is configured to engage a second surface of the sacrum different than the first surface.

17. The lead of claim 16 wherein the stent is configurable from an undeployed, compressed position to a deployed, expanded position.

18. The lead of claim 16 wherein the electrode array is disposed on the stent.

19. The lead of claim 16 wherein the stent is configured to maintain the electrode array in the foramen.

* * * * *